US00PP11538P

United States Patent [19]

Olesen et al.

[11] Patent Number: Plant 11,538

[45] Date of Patent: Oct. 3, 2000

[54] MINIATURE ROSE PLANT NAMED 'POULANIT'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/137,187

[22] Filed: Aug. 19, 1998

[51] Int. Cl.[7] ..... A01H 5/00

[52] U.S. Cl. ..... Plt./122

[58] Field of Search ..... Plt./116, 122

[56] References Cited

U.S. PATENT DOCUMENTS

P.P. 5,770 7/1986 de Ruiter ..... Plt./122

P.P. 7,021 9/1989 Meilland ..... Plt./122

P.P. 8,012 10/1992 Olesen et al. ..... Plt./122

P.P. 10,728 12/1998 Olesen et al. ..... Plt./122

OTHER PUBLICATIONS

Cairns, ed. 1993, Modern Roses 10. The American Rose Society, Shreveport, Louisiana, p. 471.

*Primary Examiner*—Howard J. Locker

[57] ABSTRACT

A new miniature rose plant which has abundant, non-fading, dark red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and an unnamed seedling. The two parents were crossed and the resulting seeds were planted in a controlled environment. The new variety is named 'POULanit'.

The new rose may be distinguished from its seed parent, an unnamed seedling, by the following combination of characteristics:

1. The unnamed seedling has a breeding background of 'POULvic', U.S. Plant Pat. No. 8,012, granted Oct. 27, 1994; and 'RUImired', U.S. Plant Pat. No. 5,770, granted Jul. 22, 1986; and 'MEIrutral', U.S. Plant Pat. No. 7,021, granted Sep. 12, 1989.

2. 'POULanit' has large double flowers, while the unnamed seedlings has small flowers.

3. 'POULanit' has dark red blooms, while the 'unnamed seedling' has clear red blooms, with a lighter color on the reverse side of the petals.

The new variety may be distinguished from its pollen parent, an unnamed seedling created by the same inventors, by the following combination of characteristics:

1. The unnamed seedling is an offspring of 'POULvic', 'POULcar' U.S. Plant Pat. No. 7,999, granted Oct. 13, 1999, and 'MEIrutral'.

2. 'POULanit' has larger flowers and foliage as compared to the unnamed seedling.

3. The flower color of 'POULanit' is a deeper red than the unnamed seedling flower color.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

As part of this rose development program, L. Pernille Olesen and Mogens N. Olesen germinated the seeds from the aforementioned hybridization and conducted evaluations on the resulting seedlings in a controlled environment in Fredensborg, Denmark.

'POULanit' was selected by the inventors as a single plant from the progeny of the hybridization in March, 1994.

Asexual reproduction of 'POULanit' by cuttings and traditional budding was first done by L. Pernille and Mogens N. Olesen in their nursery in Fredensborg, Denmark in June, 1994. This initial and other subsequent propagations conducted in controlled environments have demonstrated that the characteristics of 'POULanit' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULanit'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULanit', as observed in its growth in glasshouses in Fredensborg, Denmark; Burlington, Canada; and in a field nursery in Applegate, Jackson County, Oreg. Color references are made using The Royal Horticultural Society (London, England) Colour Chart, 1995, except where common terms of color are used.

For a comparison, the nearest existing rose variety is 'POULobe', a rose variety by the same inventors described and illustrated in U.S. Plant Pat. No. 10,728, granted Dec. 22, 1998. Chart 1 details several physical characteristics of 'POULanit' and 'POULobe'.

CHART 1

| | 'POULanit' | 'POULobe' |
|---|---|---|
| Petal color, upper surface | Red Group 46B | Red Group 44A |
| Petal color, reverse surface | Red-Purple Group 61C | Red Group 53C |
| Petal count | 20–30 petals | 35–40 petals |

Parents: Unnamed seedling×Unnamed seedling.
Classification:
*Botanical.*—*Rosa hybrida.*
*Commercial.*—Miniature.

FLOWER AND FLOWER BUD

Blooming habit: Recurrent.
Flower bud:
*Size.*—Upon opening, 18 mm–22 mm in length from base of receptacle to end of bud.
*Bud form.*—Ovoid to globular.
*Bud color.*—At ¼ opening, Red Group 53A to Red-Purple Group 61B.
*Sepals.*—Green Group 137C to 143A. Foliaceous appendages on three of the five sepals. Surfaces of other sepals slightly pubescent. All sepals with stipitate glands on exterior surface.
*Receptacle.*—Surface: Smooth, glabrous. Shape: Funnel-shaped. Size: Small to medium. 5 mm (h)×5 mm (w). Color: Green Group 143B
*Peduncle.*—Surface: With stipitate glands. Length: 25–40 mm average length. Color: Green Group 143B Strength: Upright.
*Borne.*—Generally with 1–3 buds per flowering stem.
Flower bloom:
*Size.*—Medium for a 13 cm pot rose. Average flower diameter is 45–55 mm when open.
*Form.*—Shape of flower when viewed from the side: Upon opening, upper part: Convex. Upon opening, lower part: Convex. Open flower, upper part: Flat to cupped. Open flower, lower part: Flat.
*Petalage.*—Average range: 20–30 under normal conditions.
Color:
*Petals, upon opening.*—Upper Surface: Red Group 46A-53A. Reverse Surface: Red-Purple 58A-61B.
*Petals after opening.*—Upper Surface: Red Group 46B. Reverse Surface: Red-Purple Group 61C.
Basal Petal spots: Small to average. Color uniform throughout opening.
*Petals.*—Outer side: Yellow Group 13C-13D. Inner Side: Yellow Group 13B.
General Tonality: On open flower Red Group 46A. No change in the general tonality at the end of the third day. Afterwards, general tonality is Red Group 46B.
Petals:
*Petal reflex.*—Generally straight. Outermost petals reflex backwards slightly only after bloom completely open.
*Petal edge.*—Uniform.
*Petaloids.*—Commonly none.
*Fragrance.*—Light floral scent.
*Duration.*—As a pot plant, flowers last from 8 to 12 days. As a cut flower 7 to 9 days.
*Thickness.*—Average.
*Shape.*—Round.
*Form.*—Flat to cupped.
*Arrangement.*—Regular.
*Other.*—Some petals exhibit variegations of White Group 155B.
Reproductive organs:
*Pollen.*—Color: Yellow Group 22A. Abundance: Average.
*Anthers.*—Size: Medium. Color: Yellow-Orange Group 14C. Abundance. Average.
*Filaments.*—Color: Yellow Group 1C.
*Stigmas.*—Superior in location to anthers. Color: Yellow Group 1C.
*Styles.*—Color: Yellow Group 1C.

PLANT

Plant growth: Vigorous, compact, upright to bushy. When grown as a 13 cm pot plant, the average height of the plant itself is 18 to 22 cm and the average width is 18 to 20 cm. When grown as a nursery plant (on its own roots) the average plant height is 50–60 cm and the average plant width is 50 cm.
Stems:
*Color.*—Young wood: Green Group 138A. Older wood: Green Group 138B.
*Thorns.*—Incidence: Moderate number of thorns. Size: Short, average length: 3–4 mm. Color: Yellow-Green Group 145D. Shape: Hooked downwards.
*Surface.*—Young wood: Smooth. Older wood: Smooth.
Plant foliage: Normal number of leaflets on normal leaves in middle of the stem: 5–7 leaflets.
*Leaf size.*—Medium. 75–90 mm (l)×55–65 mm (w).
*Abundance.*—Average.
*Color.*—Upper Leaf Surface: Green Group 137A-Yellow-Green Group 147A. Lower Leaf Surface: Green Group 138A-138B. Juvenile foliage:Yellow-Green Group 144A with intonations on margins and underside of leaflets of Greyed-Red Group 179A.
Plant leaves and leaflets:
*Stipules.*—Present. Size: 6 mm–8 mm. Color: Green Group 137A. Presence of hairs: Stipitate glands underneath.
*Petiole.*—Length: 12 mm–15 mm. Color: Green Group 138A. Margins: With stipitate glands. Prickles: Limited.
*Rachis.*—Color: Green Group 138A. Underneath: With prickles. Margins: Margins with stipitate glands. Prickles: Limited.
Leaflet Edge: Serrated.
Leaflet Shape: Ovate.
*Other.*—Semi-glossy finish. Average thickness.
Disease resistance: Above average resistance to mildew and Botrytis under normal growing conditions in Burlington, Canada, Applegate, Oreg., and Fredensborg, Denmark.
We claim:

1. A new and distinct variety of rose plant of the miniature class, substantially as herein illustrated and described as a distinct and novel rose variety due to its abundant, dark red flowers, vigorous and compact growth, year round flowering under glasshouse conditions, suitability for production from softwood cuttings in pots, and durable flowers and foliage which make the variety suitable for distribution in the floral industry.

* * * * *

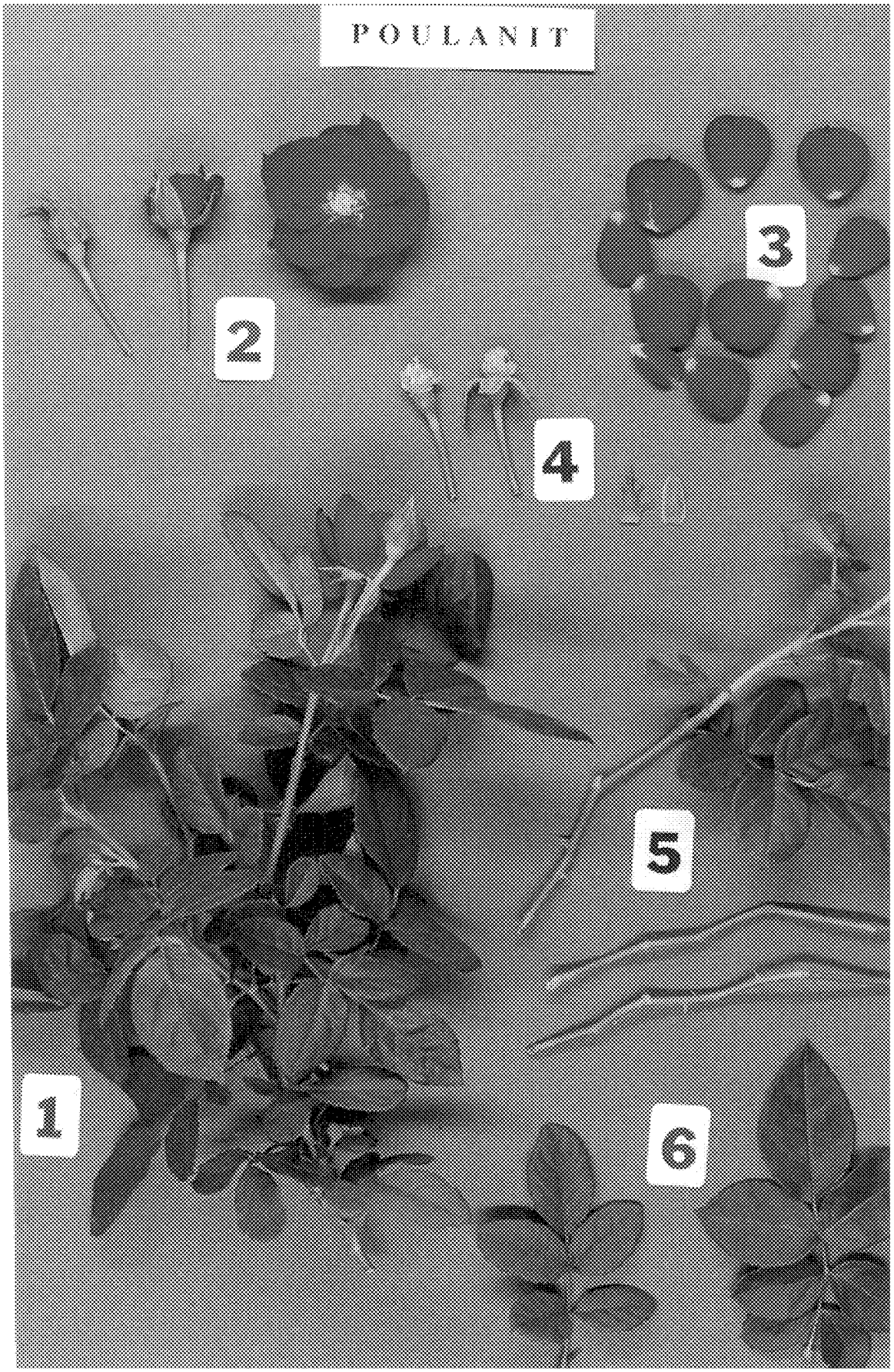
POULANIT
1
2
3
4
5
6